United States Patent
Larsson et al.

(10) Patent No.: US 10,710,047 B2
(45) Date of Patent: Jul. 14, 2020

(54) CORROSION RESISTANT DUPLEX STEEL ALLOY, OBJECTS MADE THEREOF, AND METHOD OF MAKING THE ALLOY

(71) Applicant: Stamicarbon B.V., Sittard (NL)

(72) Inventors: Linn Larsson, Järbo (SE); Daniel Gullberg, Gävle (SE); Ulf Kivisäkk, Sandviken (SE); Martin Östlund, Gävle (SE); Alexander Aleida Antonius Scheerder, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 16/024,686

(22) Filed: Jun. 29, 2018

(65) Prior Publication Data
US 2018/0304224 A1    Oct. 25, 2018

Related U.S. Application Data

(63) Continuation of application No. 15/108,549, filed as application No. PCT/NL2014/050902 on Dec. 23, 2014, now Pat. No. 10,046,297.

(30) Foreign Application Priority Data

Dec. 27, 2013    (EP) .................................... 13199704

(51) Int. Cl.
*B01J 19/02*    (2006.01)
*B22F 3/15*    (2006.01)
(Continued)

(52) U.S. Cl.
CPC ................ *B01J 19/02* (2013.01); *B22F 3/15* (2013.01); *C07C 273/04* (2013.01);
(Continued)

(58) Field of Classification Search
CPC .. B01J 19/02; B01J 2219/02; B01J 2219/025; B01J 2219/0277; B01J 2219/0286;
(Continued)

(56) References Cited

U.S. PATENT DOCUMENTS 4,581,202 A    4/1986 Kudo
5,582,656 A    12/1996 Kangas et al.
(Continued)

FOREIGN PATENT DOCUMENTS

EP    0 692 547    1/1996
WO    WO-95/00674    1/1995
(Continued)

OTHER PUBLICATIONS

Communication pursuant to Article 94(3) EPC for EP 14 825 467.5, dated Oct. 6, 2017, 3 pages.
(Continued)

*Primary Examiner* — Natasha E Young
(74) *Attorney, Agent, or Firm* — Morrison & Foerster LLP

(57) ABSTRACT

Disclosed is a Hot Isostatic Pressed ferritic-austenitic steel alloy, as well objects thereof. The elementary composition of the alloy comprises, in percentages by weight:

| | |
|---|---|
| C | 0-0.05; |
| Si | 0-0.8; |
| Mn | 0-4.0; |
| Cr | more than 29-35; |
| Ni | 3.0-10; |
| Mo | 0-4.0; |
| N | 0.30-0.55: |
| Cu | 0-0.8; |
| W | 0-3.0; |
| S | 0-0.03; |
| Ce | 0-0.2; |

(Continued)

the balance being Fe and unavoidable impurities. The objects can be particularly useful in making components for a urea production plant that require processing such as machining or drilling. A preferred use is in making, or replacing, liquid distributors as used in a stripper as is typically present in the high-pressure synthesis section of a urea plant.

16 Claims, 6 Drawing Sheets

(51) Int. Cl.
  *C07C 273/04*    (2006.01)
  *C22C 33/02*    (2006.01)
  *C22C 38/00*    (2006.01)
  *C22C 38/02*    (2006.01)
  *C22C 38/04*    (2006.01)
  *C22C 38/40*    (2006.01)
  *C22C 38/42*    (2006.01)
  *C22C 38/44*    (2006.01)
  *C22C 38/58*    (2006.01)
  *F28F 21/08*    (2006.01)

(52) U.S. Cl.
  CPC ........ *C22C 33/0285* (2013.01); *C22C 38/002* (2013.01); *C22C 38/005* (2013.01); *C22C 38/02* (2013.01); *C22C 38/04* (2013.01); *C22C 38/40* (2013.01); *C22C 38/42* (2013.01); *C22C 38/44* (2013.01); *C22C 38/58* (2013.01); *F28F 21/083* (2013.01); *B01J 2219/0286* (2013.01)

(58) Field of Classification Search
  CPC ...... B22F 3/00; B22F 3/12; B22F 3/14; B22F 3/15; C07C 273/00; C07C 273/02; C07C 273/04; C22C 33/00; C22C 33/02; C22C 33/0257; C22C 33/0278; C22C 33/0285; C22C 38/00; C22C 38/002; C22C 38/005; C22C 38/02; C22C 38/04; C22C 38/18; C22C 38/40; C22C 38/42; C22C 38/44; C22C 38/58; F28F 21/00; F28F 21/08–083

See application file for complete search history.

(56) References Cited

U.S. PATENT DOCUMENTS

| | | | |
|---|---|---|---|
| 6,793,119 B2 * | 9/2004 | Eijkenboom | ........ B23K 35/383 |
| | | | 228/119 |
| 7,347,903 B2 | 3/2008 | Yamadera et al. | |
| 8,158,824 B2 * | 4/2012 | Gevers | ................. C07C 273/04 |
| | | | 564/67 |
| 2013/0129556 A1 * | 5/2013 | Didomizio | ................ B22F 3/15 |
| | | | 419/19 |

FOREIGN PATENT DOCUMENTS

| | | |
|---|---|---|
| WO | WO-2011/162610 | 12/2011 |
| WO | WO-2013/064746 | 5/2013 |
| WO | WO-2013/165247 | 11/2013 |

OTHER PUBLICATIONS

Communication under rule 71(3) EPC for EP 14 825 467.5, dated May 9, 2018, 7 pages.
International Search Report for PCT/NL2014/050902, dated Apr. 13, 2015, 4 pages.
Ullmann's Encyclopedia of Industrial Chemistry, Fifth, Completely Revised Edition, Elvers and Hawkins (eds.), VCH Verslagsgesellschaft mbH, Germany (1996) vol. A27, pp. 333-350.

* cited by examiner (a)  (b)

CORROSION RESISTANT DUPLEX STEEL ALLOY, OBJECTS MADE THEREOF, AND METHOD OF MAKING THE ALLOY

CROSS-REFERENCE TO RELATED APPLICATIONS

This application is a continuation of U.S. Ser. No. 15/108,549, now U.S. Pat. No. 10,046,297, having an international filing date of 23 Dec. 2014, which is the national phase of PCT application PCT/NL2014/050902, published as WO 2015/099530, having an international filing date of 23 Dec. 2014, which claims benefit of European patent application No. 13199704.1 filed 27 Dec. 2013. The contents of the above patent applications are incorporated by reference herein in their entirety.

FIELD OF THE INVENTION

The invention pertains to corrosion resistant duplex steel (ferritic austenitic steel) alloys. Particularly, the invention pertains to objects made of said alloy, and to a process for producing said alloy. Further, the invention pertains to a urea plant comprising components made from said alloy, and to a method of modifying an existing urea plant.

BACKGROUND OF THE INVENTION

Duplex stainless steel refers to ferritic austenitic steel alloy. Such steels have a microstructure comprising ferritic and austenitic phases. The duplex steel alloy, to which the invention pertains, is characterized by a high content of Cr and N and a low content of Ni. Background references in this respect include WO 95/00674 and U.S. Pat. No. 7,347,903. The duplex steels described therein are highly corrosion resistant and can therefore be used, e.g., in the highly corrosive environment of a urea manufacturing plant.

Urea ($NH_2CONH_2$) can be produced from ammonia and carbon dioxide at elevated temperature (typically between 150° C. and 250° C.) and pressure (typically between 12 and 40 MPa) in the urea synthesis section of a urea plant. In this synthesis, two consecutive reaction steps can be considered to take place. In the first step, ammonium carbamate is formed, and in the next step, this ammonium carbamate is dehydrated so as to provide urea, The first step (i) is exothermic, and the second step can be represented as an endothermic equilibrium reaction (ii):

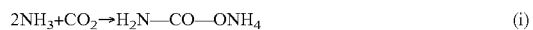

$$2NH_3 + CO_2 \rightarrow H_2N-CO-ONH_4 \qquad (i)$$

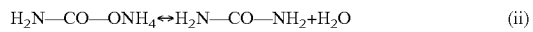

$$H_2N-CO-ONH_4 \leftrightarrow H_2N-CO-NH_2 + H_2O \qquad (ii)$$

In a typical urea production plant, the foregoing reactions are conducted in a urea synthesis section so as to result in an aqueous solution comprising urea. In one or more subsequent concentration sections, this solution is concentrated to eventually yield urea in the form of a melt rather than a solution. This melt is further subjected to one or more finishing steps, such as prilling, granulation, pelletizing or compacting.

A frequently used process for the preparation of urea according to a stripping process is the carbon dioxide stripping process, as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and, preferably but not necessarily, a scrubber in which the operating pressure is in between 12 and 18 MPa, such as in between 13 and 16 MPa. In the synthesis section, the urea solution leaving the urea reactor is fed to a stripper in which a large amount of non-converted ammonia and carbon dioxide is separated from the aqueous urea solution.

Such a stripper can be a shell- and tube-heat exchanger in which the urea solution is fed to the top part at the tube side and a carbon dioxide feed, for use in urea synthesis, is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide, inert gases and a small amount of water.

Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The formed solution, which contains condensed ammonia, carbon dioxide, water and urea, is recirculated together with the non-condensed ammonia, carbon dioxide and inert vapor.

The processing conditions are highly corrosive, particularly due to the hot carbamate solution. In the past, this presented a problem in the sense that the urea manufacturing equipment, even though made from stainless steel, would corrode and be prone to early replacement.

This has been resolved, particularly by making the equipment, i.e. the relevant parts thereof subjected to the mentioned corrosive conditions, from a duplex steel described in WO 95/00674 (also known by the trademark of Safurex®). However, even though the foregoing reflects a major advancement in urea production, a particular problem exists in the stripper. A typical carbamate stripper comprises a plurality (several thousand) of tubes. Through the tubes, a liquid film runs downwards whilst stripping gas (typically $CO_2$) runs upwards. Provisions are generally made to ensure that all tubes have the same load of liquid so as to have a flow of the liquid at the same speed. For, if the liquid does not flow through all of the tubes at the same speed, the efficiency of the stripper is reduced. These provisions comprise a liquid distributor, generally in the form of a cylinder with small holes in it.

It has been experienced that the liquid distributors need a relatively frequent replacement. Particularly, the size and shape of the holes changes with time, apparently as a result of corrosion, despite the fact that the liquid distributors are made from corrosion-resistant duplex steel as mentioned above. Thus, the affected distributors result in a different throughput of liquid in the stripper, as a result of which the desired equal loading of the stripper's tubes is less efficient.

It is therefore desired in the art to provide a corrosion resistant material that would provide the liquid distributors in the stripper with a better corrosion endurance.

SUMMARY OF THE INVENTION

In order to address one or more of the foregoing desires, the present invention, in one aspect, provides a ferritic-austenitic steel alloy, the elementary composition of which comprises, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities; wherein the austenite spacing, as determined by DNV-RP-F112, Section 7, using the sample preparation according to ASTM E 3-01, is smaller than 20 µm, such as smaller than 15 µm, such as in the range of from 8-15 µm on a sample; and wherein the largest average austenite phase length/width ratio selected from the average austenite phase length/width ratio determined in three cross-sections of a sample as needed, the cross-sections taken at three perpendicular planes of a sample is smaller than 5, such as smaller than 3, such as smaller than 2;

the average austenite, phase length/width ratio being determined by the following procedure:

i. preparing the cross-cuts surfaces of the sample;

ii. polishing the surfaces using diamond paste on a rotating disc with a particle size of first 6 µm and subsequently 3 µm to create a polished surface;

iii. etching the surfaces using Murakami's agent for up to 30 seconds at 20° C. thereby coloring the ferrite phase, the agent being provided by preparing a saturated solution by mixing 30 g potassium hydroxide and 30 g $K_3Fe(CN)_6$ in 100 ml $H_2O$, and allowing the solution to cool down to room temperature before use;

iv. observing the cross-cut surfaces in etched condition under an optical microscope with a magnification selected such that phase boundaries are distinguishable;

v. projecting a cross-grid over the image, wherein the grid has a grid distance adapted to observe the austenite-ferrite phase boundaries;

vi. randomly selecting at least ten grid crossings on the grid such that the grid crossings can be identified as being in the austenite phase;

vii. determining, at each of the ten grid crossings, the austenite phase length/width ratio by measuring the length and the width of the austenite phase, wherein the length is the longest uninterrupted distance when drawing a straight line between two points at the phase boundary, the phase boundary being the transition from an austenitic phase to the ferrite phase; and wherein the width is defined as the longest uninterrupted distance measured perpendicular to the length in the same phase;

viii. calculating the average austenite phase length/width ratio as the numerical average of the austenite phase length/width ratios of the ten measured austenite phase length/width ratios.

In one embodiment of the present invention the sample on which the measurement is performed has at least one dimension, such as length, width, or height, greater than 5 mm.

In another aspect, the invention presents a formed object obtainable by subjecting a ferritic-austenitic alloy powder to hot isostatic pressing, wherein the ferritic-austenitic alloy powder comprises, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities.

In yet another aspect, the invention relates to the use of a ferritic-austenitic alloy as defined hereinabove or hereinafter as a construction material for a component for a urea manufacturing plant, wherein the component is intended to be in contact with a carbamate solution, and wherein the components comprise one or more machined or drilled surfaces.

In a still further aspect, the invention provides a method of manufacturing an object of a corrosion-resistant ferritic-austenitic alloy, the method comprising the steps of:

a. melting a ferritic-austenitic alloy comprising, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities;

b. atomizing the melt to produce a powder with a mean particle size in the range of about 100-150 µm and a maximum particle size of about 500 µm;

c. providing a mold defining the shape of the object to be produced;

d. filling at least a portion of the mold with the powder;

e. submitting said mold, as filled under d, to Hot Isostatic Pressing (HIP) at a predetermined temperature, a predetermined pressure and for a predetermined time so that the particles of said powder bond metallurgically to each other to produce the object.

In a further aspect, the invention relates to a liquid distributor for a carbamate stripper in a urea manufacturing plant, the liquid distributor being an object as described above.

In another aspect, the invention relates to a plant for the production of urea, said plant comprising a high pressure urea synthesis section comprising a reactor, a stripper, and a condenser, wherein the stripper comprises liquid distributors as described above.

In a still further aspect, the invention provides a method of modifying an existing plant for the production of urea, said plant comprising a stripper having tubes and liquid distributors made from a corrosion-resistant ferritic-austenitic alloy comprising, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities; the method comprising replacing the liquid distributors by liquid distributors as described above.

DETAILED DESCRIPTION OF THE INVENTION

Figure 1:
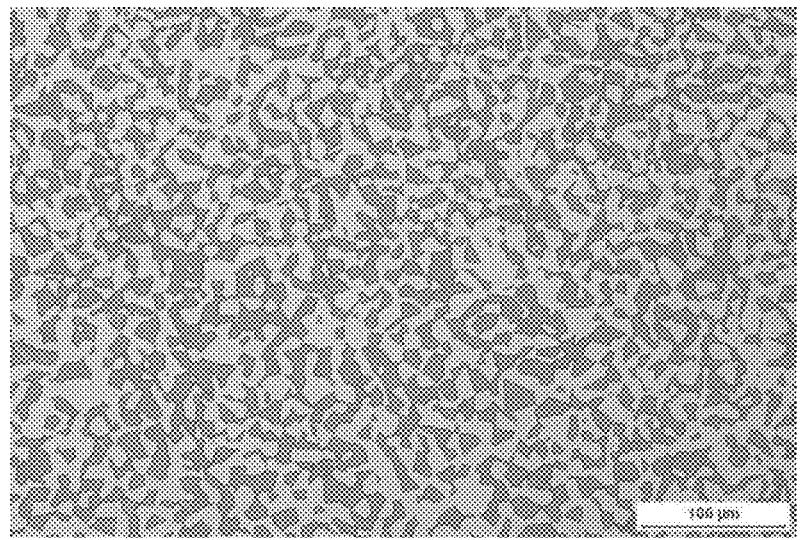
FIG. 1 to FIG. 5 are microscopic pictures of test specimens referred to in Example 1.
Figure 1:
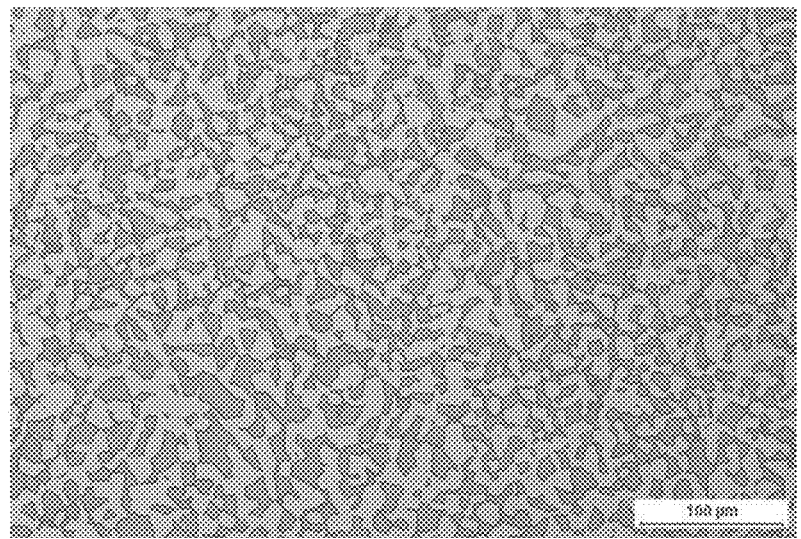
Figure 1:
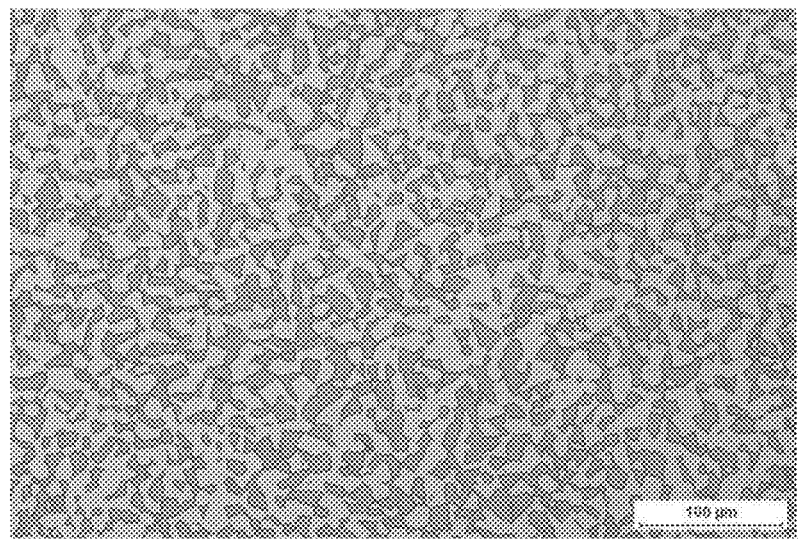
Figure 2:
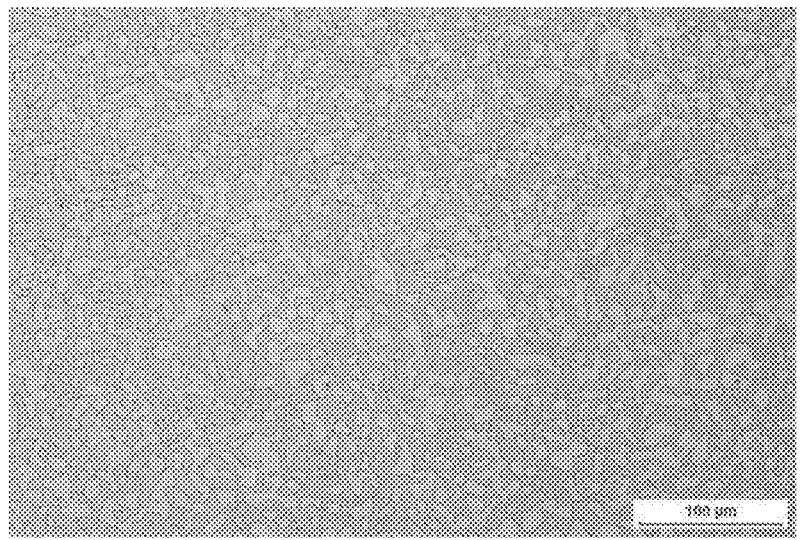
Figure 2:
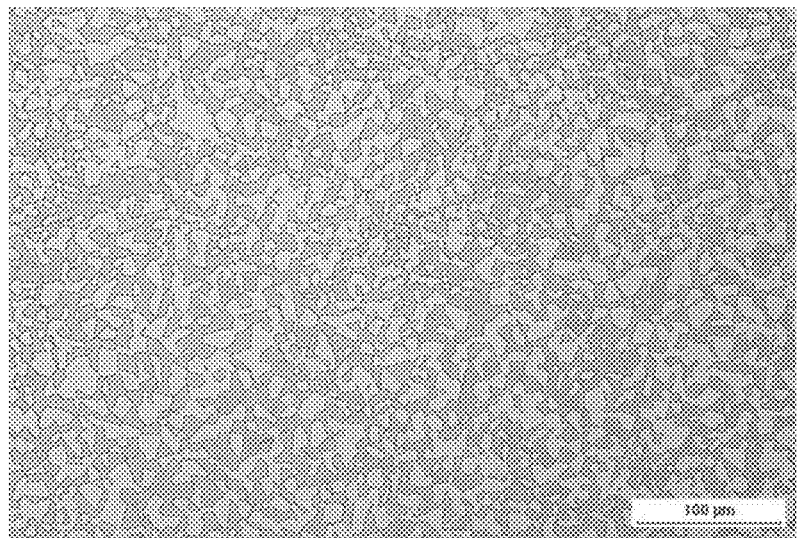
Figure 2:
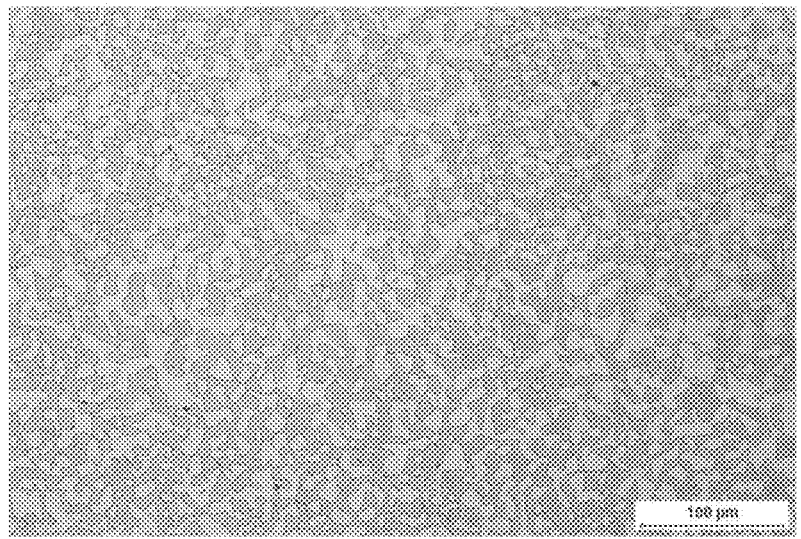
Figure 3:
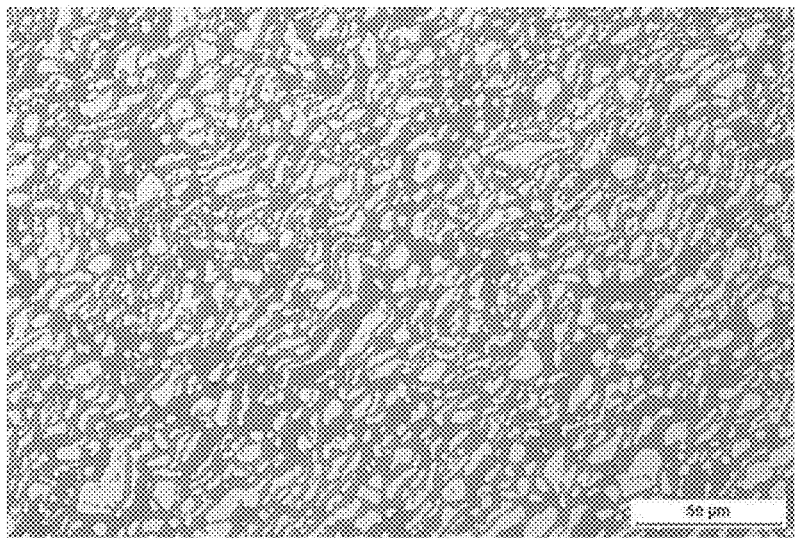
Figure 3:
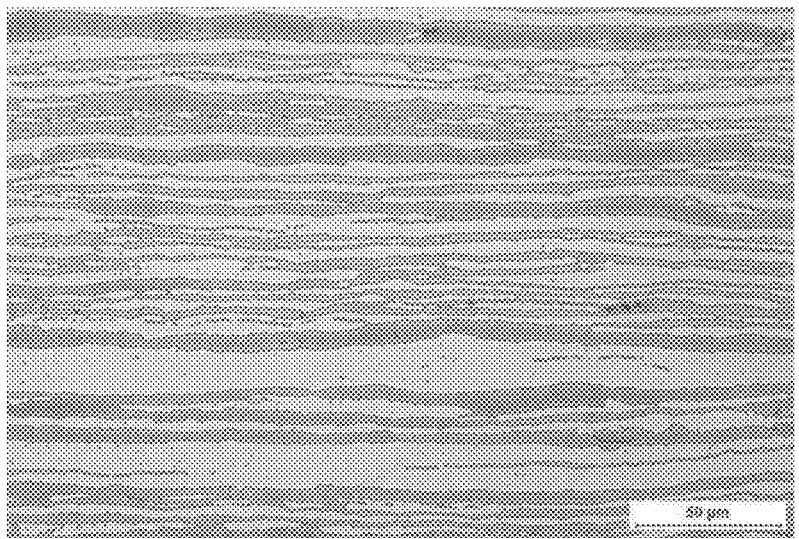
Figure 3:
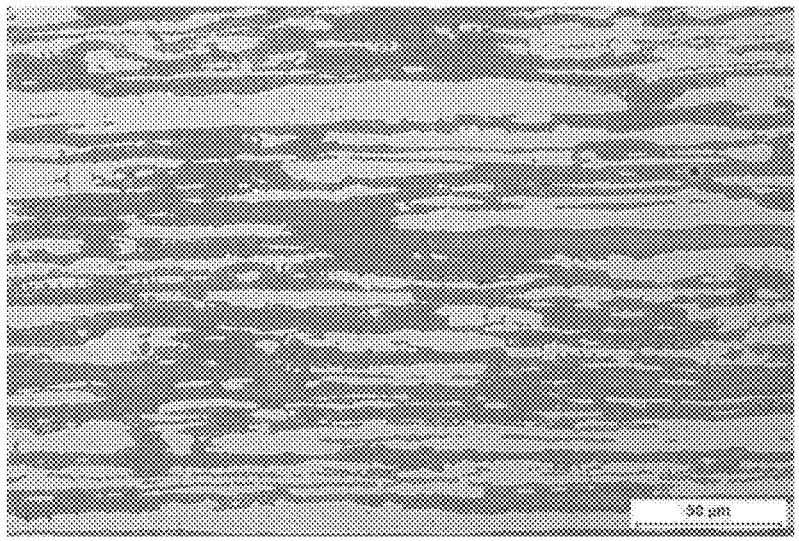
Figure 4:
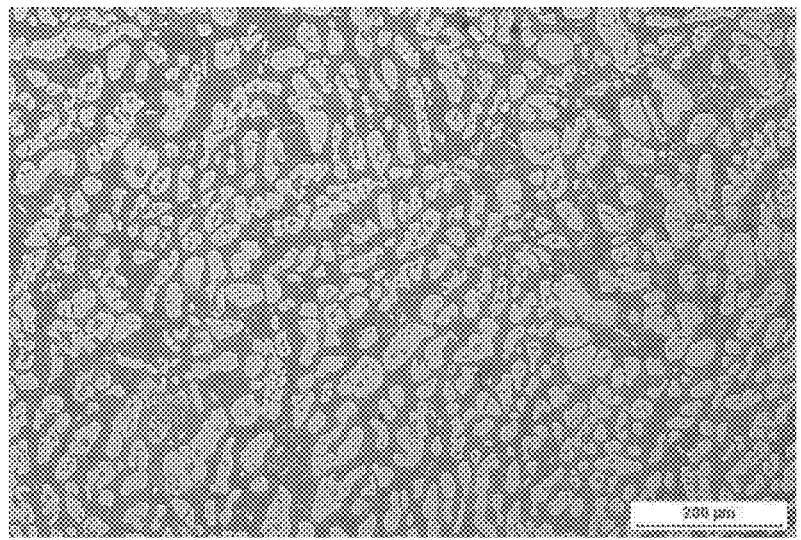
Figure 4:
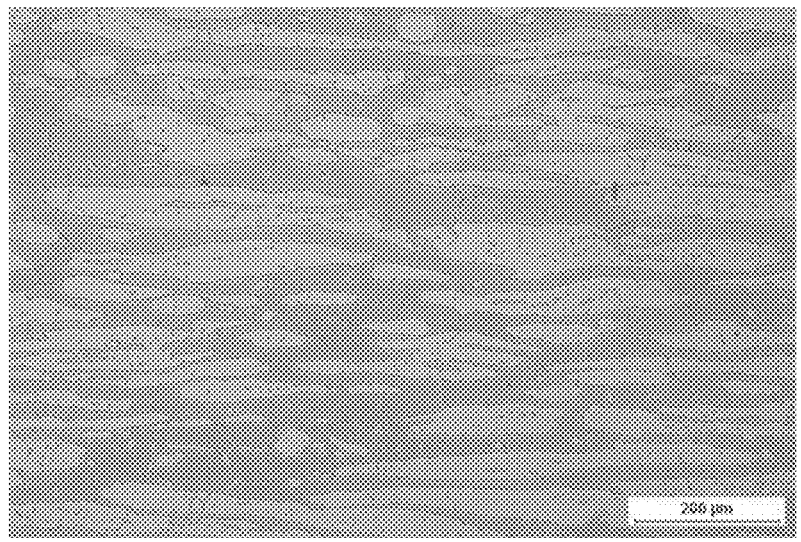
Figure 4:
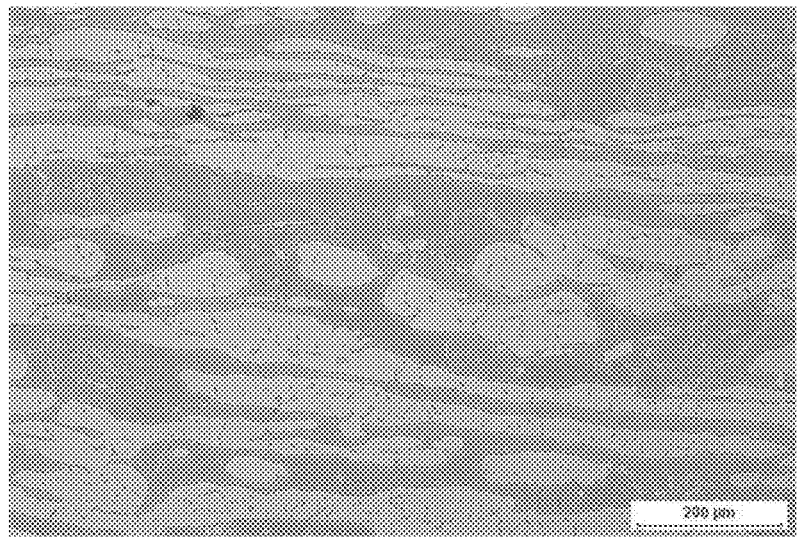
Figure 5:
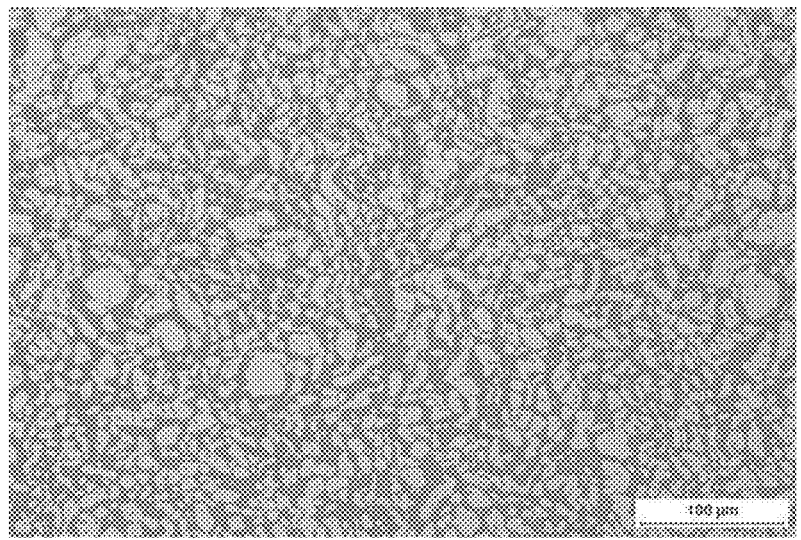
Figure 5:
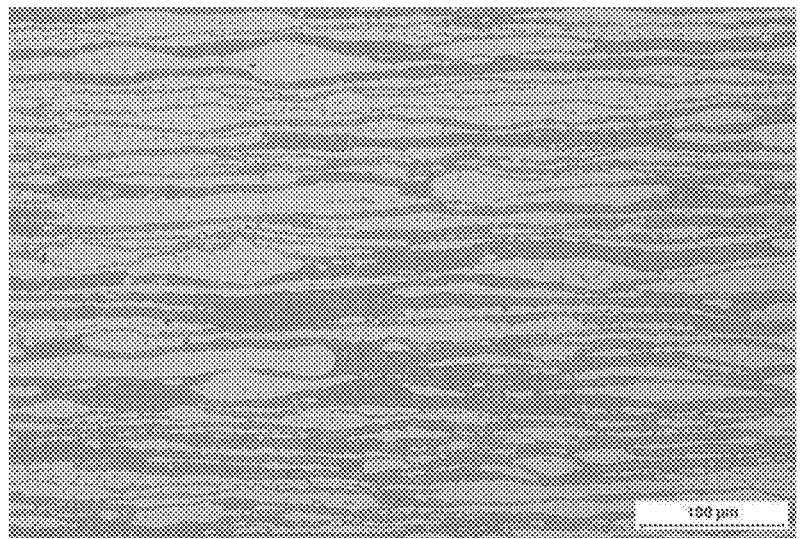
Figure 5:
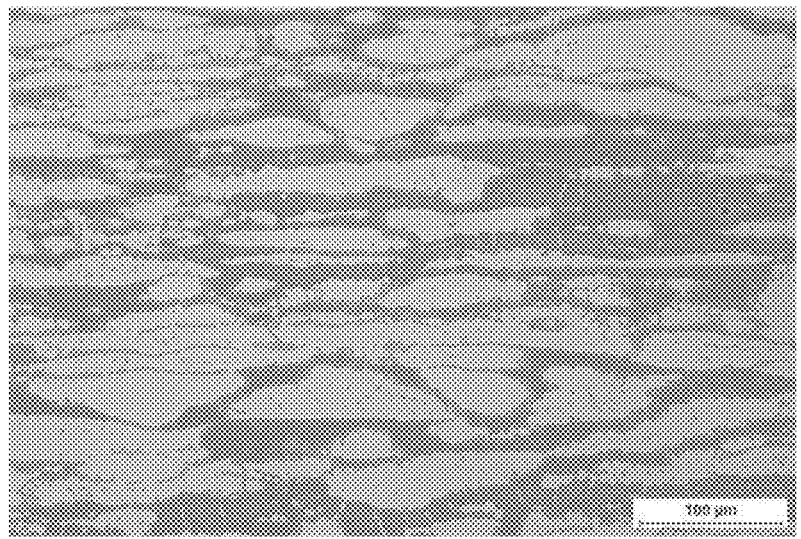

In a broad sense, the invention based on the judicious insight that the still occurring corrosion in the liquid distributors in a urea stripper, is affected by cross-cut end attack. This refers to corrosion taking place at a surface created by making a cross-cut. This type of corrosion is different from other types of corrosion, such as fatigue corrosion (mechanical fatigue in a chemical environment), chloride stress corrosion cracking, erosion corrosion (particle abrasion in chemical environment), crevice corrosion or pitting corrosion.

The inventors came to the surprising finding that by manufacturing components from HIPed ferritic-austenitic alloy which alloy is defined hereinabove or hereinafter, any cross cut surface created in the said component either by drilling or machining operation will have reduced and/or eliminated vulnerability to cross-cut end-attack.

The inventors also came to the surprising finding that the overall weight loss of said components as a result of corrosion is significantly less compared to identical components made of similar ferritic-austenitic steel but not produced via the HIP method (i.e. via hot extrusion followed by cold working). It has been found that the HIPed material will be isotropic as to the distribution and shape of the phases (or microstructure). It will be understood that the material is necessarily anisotropic on a microscale due to the two-phase nature of the duplex steel. Also, in HIPed material, a single grain is anisotropic due to its crystal structure. A large selection of grains with random orientation will be isotropic on a meso- or macroscale.

These scales can be understood to relate to the size of the austenite spacing. In a HIPed duplex component, said spacing is generally between 8-15 um.

The ferritic-austenitic alloy and the objects, in the present invention are obtainable by subjecting a ferritic-austenitic steel alloy powder to hot isostatic pressing, wherein the ferritic-austenitic steel powder comprises, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities.

The alloy, and objects, so obtainable can be particularly characterized with reference to the austenite spacing and average austenite phase length/width ratio, as indicated above.

In the described experiments, inter alia, an optical microscope is used for observing the cross-cut surfaces in etched condition of a sample. The microscope can be any optical microscope suitable for metallographic examinations. The magnification is selected so that phase boundaries are distinguishable. The skilled person will normally be able to assess whether phase boundaries are visible, and will thus be able to select the appropriate magnification. According to DNV RP F112, a magnification should be selected such that 10-15 micro-structural units are intersected by each line (a straight line drawn through the image). A typical magnification is 100×-400×.

In the experiments, a cross-grid is projected over the image, wherein the grid has a grid distance adapted to observe the austenite-ferrite phase boundaries. Typically, 20-40 grid crossings are provided.

The ferritic-austenitic steel alloy can be made in accordance with the disclosures in WO 05/00674 or U.S. Pat. No. 7,347,903. The skilled reader will be able to produce the steel alloys with reference to these disclosures. Additionally, the content of these disclosures is hereby incorporated by reference.

The elementary composition of the ferritic-austenitic steel alloy is generally as defined hereinabove or hereinafter.

Carbon (C) is to be considered rather as an impurity element in the present invention and has a limited solubility in both ferrite and austenite phase. This limited solubility implies that a risk for carbide precipitations exists at too high percentages, with decreased corrosion resistance as a consequence. Therefore, the C-content should be restricted to maximally 0.05 wt %, such as maximally (103 wt %, such as maximally 0.02 wt %.

Silicon (Si) is used as a desoxidation additive at steel manufacture. However, too high Si content increases the tendency for precipitations of intermetallic phases and decreases the solubility of N. For this reason the Si content should be restricted to max. 0.8 wt %, such as max. 0.6 wt %, such as in the range of from 0.2-0.6 wt %, such as max 0.5 wt %.

Manganese (Mn) is added to increase the solubility of N and for replacing Ni as an alloying element as Mn is considered to be austenite-stabilizing. Suitably, a Mn content of between 0 and 4.0 wt % is chosen, such as between 0.8-1.50 wt %, such as 0.3-2.0 wt %, such as 0.3-1.0 wt %.

Chromium (Cr) is the most active element for increasing the resistance against most types of corrosion. At urea synthesis the Cr content is of great importance for the resistance, wherefore the Cr content should be maximized as far as possible out of a structure stability point of view. In order to attain sufficient corrosion resistance in the austenite, the Cr content should be in the range of from 26-35 wt %, such as in the range of from 28-30 wt %, such as in the range of from 29-33 wt %. In an interesting embodiment of the invention, the Cr content is more than 29%, such as more than 29-33, such as more than 29 to 30. In another interesting embodiment, the Cr content is more than 29.5%, such as more than 29.5-33, such as more than 29.5 to 31, such as more than 29.5 to 30.

Nickel (Ni) is mainly used as an austenite stabilizing element and its content should be kept as low as possible. An important reason for the bad resistance of austenitic stainless steels in urea environments with low contents of oxygen is supposed to be their relatively high content of Ni. In the present invention, a content of from 3-10 wt % Ni is required, such as 3-7.5 wt % Ni, such as 4-9 wt %, such as 5-8 wt %, such as 6-8 wt. %, in order to attain a ferrite content in the range of from 30-70% by volume.

Molybdenum (Mo) is used to improve the passivity of the alloy. Mo together with Cr and N are those elements that most effectively increase the resistance against pitting and crevice corrosion. Further, Mo diminishes the tendency for precipitations of nitrides by increasing the solid solubility of N. However, too high content of Mo involves the risk of precipitations of intermetallic phases. Therefore, the Mo content should be in the range of from 0 to 4.0 wt %, such as of from 1.0 to 3 wt %, such as of from 1.50 to 2.60 wt %, such as of from 2-2.6 wt. %.

Nitrogen (N) is a strong austenite former and enhances the reconstitution of austenite. Additionally, N influences the distribution of Cr and Mo so that higher content of N increases the relative share of Cr and Mo in the austenite phase. This means that the austenite becomes more resistant to corrosion, also that higher contents of Cr and Mo may be included into the alloy while the structure stability is maintained. However, it is well known that N suppresses the formation of intermetallic phase, also in fully austenitic steels. Therefore, N should be in the range of from 0.30 to 0.55 wt %, such as of from 0.30 to 0.40 wt %, such as of from 0.33 to 0.55 wt %, such as of from 0.36 to 0.55 wt %.

Copper (Cu) improves the general corrosion resistance in acid environments, such as sulfuric acid. However, high content of Cu will decrease the pitting and crevice corrosion resistance. Therefore, the content of Cu should be restricted to max. 1.0 wt %, such as max. 0.8 wt %. In an interesting embodiment of invention, the Cu content particularly is maximally 0.8%.

Tungsten (W) increases the resistance against pitting and crevice corrosion. But too high content of W increases the risk for precipitation of intermetallic phases, particularly in combination with high contents of Cr and Mo. Therefore, the amount of W should be limited to max. 3.0 wt %, such as max. 2.0 wt %.

Sulfur (S) influences the corrosion resistance negatively by the formation of easily soluble sulfides. Therefore, the content of S should be restricted to max. 0.03 wt %, such as max. 0.01 wt %, such as max. 0.005 wt %, such as max. 0.001 wt %.

Cerium may be added to the ferritic-austenitic alloy in percentages up to max. 0.2 wt %.

The ferrite content of the ferritic-austenitic alloy according to the present invention is important for the corrosion resistance. Therefore, the ferrite content should be in the range of from 30% to 70% by volume, such as in the range of from 30 to 60 vol. %, such as in the range of from 30 to 55 vol. %, such as in the range of from 40 to 60 vol. %.

When the term "max" is used, the skilled person knows that the lower limit of the range is 0 wt % unless another number is specifically stated.

According to the present invention, another composition comprises, in percentages by weight:

| | |
|---|---|
| C | max. 0.03; |
| Mn | 0.8-1.50; |
| S | max. 0.03; |
| Si | max. 0.50; |
| Cr | 28-30; |
| Ni | 5.8-7.5; |
| Mo | 1.50-2.60; |
| Cu | max. 0.80; |
| N | 0.30-0.40; |
| W | 0-3.0; |
| Ce | 0-0.2; | and the balance Fe and unavoidable impurities;

Yet another composition according to the present invention comprises, in percentages by weight:

| | |
|---|---|
| C | max. 0.03; |
| Si | max. 0.8; such as 0.2-0.6; |
| Mn | 0.3-2; such as 0.3-1; |
| Cr | 29-33; |
| Ni | 3-10; such as 4-9; such as 5-8; such as 6-8; |
| Mo | 1-3; such as 1-1.3; such as 1.5-2.6; such as 2-2.6; |
| N | 0.36-0.55; |
| Cu | max. 1.0; |
| W | max. 2.0; |
| S | max. 0.03; |
| Ce | 0-0.2; | the remainder being Fe and unavoidable impurities, the ferrite content being 30-70% by volume, such as in the range of from 30 to 60 vol. %, such as in the range of from 30 to 55 vol. %, such as in the range of from 40 to 60 vol. %.

In an interesting embodiment, the invention refers to a ferritic-austenitic steel alloy, the elementary composition of which consists of, in percentages by weight:

| | |
|---|---|
| C | 0-0.05; |
| Si | 0-0.8; |
| Mn | 0-4.0; |
| Cr | more than 29-35; |
| Ni | 3.0-10; |
| Mo | 0-4.0; |
| N | 0.30-0.55; |
| Cu | 0-0.8; |
| W | 0-3.0; |
| S | 0-0.03; |
| Ce | 0-0.2; | the balance being Fe and unavoidable impurities;

wherein the austenite spacing, as determined on a sample by DNV-RP-F112, Section 7, using the sample preparation according to ASTM E 3-01, is smaller than 20 μm; and wherein the largest average austenite phase length/width ratio selected from the average austenite phase length/width ratio determined in three cross-sections of a sample as needed, the cross-sections taken at three perpendicular planes of a sample is smaller than 5;

the average austenite phase length/width ratio being determined by the following procedure:

i. preparing the cross-cuts surfaces of the sample;

ii. polishing the surfaces using diamond paste on a rotating disc with a particle size of first 6 μm and subsequently 3 μm to create a polished surface;

iii. etching the surfaces using Murakarni's agent for up to 30 seconds at 20° C. thereby coloring the ferrite phase, the agent being provided by preparing a saturated solution by mixing 30 g potassium hydroxide and 30 g K3Fe(CN)6 in 100 ml H2O, and allowing the solution to cool down to room temperature before use;

iv. observing the cross-cut surfaces in etched condition under an optical microscope with a magnification selected such that phase boundaries are distinguishable;

v. projecting a cross-grid over the image, wherein the grid has a grid distance adapted to observe the austenite-ferrite phase boundaries;

vi. randomly selecting at least ten grid crossings on the grid such that the grid crossings can be identified as being in the austenite phase;

vii. determining, at each of the ten grid crossings, the austenite phase length/width ratio by measuring the length and the width of the austenite phase, wherein the length is the longest uninterrupted distance when drawing a straight line between two points at the phase boundary, the phase boundary being the transition from an austenitic phase to the ferrite phase; and wherein the width is defined as the longest uninterrupted distance measured perpendicular to the length in the same phase;

calculating the average austenite phase length/width ratio as the numerical average of the austenite phase length/width ratios of the ten measured austenite, phase length/width ratios;

and wherein the sample on which the measurement is performed has at least one dimension greater than 5 mm.

In an embodiment hereof, the elementary composition comprises, in percentages by weight:

| | |
|---|---|
| C | 0-0.030; |
| Mn | 0.8-1.50; |
| S | 0-0.03; |
| Si | 0-0.50; |
| Cr | more than 29-30.0; |
| Ni | 5.8-7.5; |
| Mo | 1.50-2.60; |
| W | 0-3.0 |
| Cu | 0-0.80; |
| N | 0.30-0.40 |
| Ce | 0-0.2; | the balance Fe and unavoidable impurities.

In a further embodiment the elementary composition comprises, in percentages by weight:

| | |
|---|---|
| C | 0-0.03; |
| Si | 0-0.5; |
| Mn | 0.3-1; |
| Cr | more than 29-33; |
| Ni | 3-10; |
| Mo | 1.0-1.3; |
| N | 0.36-0.55; |
| Cu | 0-0.8; |
| W | 0-2.0; |
| S | 0-0.03; |
| Ce | 0-0.2; | the remainder being Fe and unavoidable impurities.

In an interesting embodiment the invention provides an object obtainable by subjecting a ferritic-austenitic steel (duplex steel) alloy powder to hot isostatic pressing, wherein the duplex steel powder comprises, in percentages by weight:

| | |
|---|---|
| C | 0-0.05; |
| Si | 0-0.8; |
| Mn | 0-4.0; |
| Cr | more than 29-35; |
| Ni | 3.0-10; |
| Mo | 0-4.0; |
| N | 0.30-0.55; |
| Cu | 0-0.8; |
| W | 0-3.0; |
| S | 0-0.03; |
| Ce | 0-0.2; | the balance being Fe and unavoidable impurities;

Hot Isostatic Pressing (HIP) is a technique known in the alt. As the skilled person is aware, for the duplex steel alloy to be subjected to hot isostatic pressing, it has to be provided in the form of a powder. Such powder can be created by atomizing hot alloy, i.e. by spraying the hot alloy through a nozzle whilst in a liquid state (thus forcing molten alloy through an orifice) and allowing the alloy to solidify immediately thereafter. Atomization is conducted at a pressure known to the skilled person as the pressure will depend on the equipment used for performing atomization. Preferably, the technique of gas atomization is employed, wherein a gas is introduced into the hot metal alloy stream just before it leaves the nozzle, serving to create turbulence as the entrained gas expands (due to heating) and exits into a large collection volume exterior to the orifice. The collection volume is preferably filled with gas to promote further turbulence of the molten metal jet.

The $D_{50}$ of the size distribution of the particles is usually of from 80-130 μm.

The resulting powder is then transferred to a mold (i.e. a form defining the shape of an object to be produced). A desired portion of the mold is filled, and the filled mold is subjected to Hot Isostatic Pressing (HIP) so that the particles of said powder bond metallurgically to each other to produce the object. The HIP method according to the invention is performed at a predetermined temperature, below the melting point of the ferritic austenitic alloy, preferably in the range of from 1000-1200° C. The predetermined isostatic pressure is ≥900 bar, such as about 1000 bar and the predetermined time is in the range of from 1-5 hours.

In accordance with the invention, the HIP process according to the present disclosure may also be followed by heat treatment, such as treating the obtained object at a temperature range of from 1000-1200° C. for 1-5 h with subsequent quenching.

At least part of the mold is to be filled, depending on whether or not the entire object is made in a single HIP step. According to one embodiment, the mold is fully filled, and the object is made in a single HIP step. After the HIP, the object is removed from the mold. Usually this is done by removing the mold itself, e.g. by machining or pickling.

The form of the object obtained is determined by the form of the mold, and the degree of filling of the mold. Preferably, the mold is made such as to provide the desired end-shape of the object. E.g., if a tubular liquid distributor is to be made, the mold will serve to define a tube. The aforementioned holes to be made into the liquid distributor can be suitably made by drilling afterwards. Without wishing to be bound by theory, the inventors believe that due to the isotropy of the specific HIP material as defined hereinabove or hereinafter, the holes will be as corrosion-resistant as the rest of the duplex alloy parts.

Thus, the present HIP method may be described accordingly:

In a first step, a form (mould, capsule) is provided defining at least a portion of the shape or contour of the final object. The form is typically manufactured from steel sheets, such as carbon steel sheets, which are welded together. The form may have any shape and may be sealed by welding after filling of the form. The form may also define a portion of the final component. In that case, the form may be welded to a pre-manufactured component, for example a forged or cast component. The form does not have to have the final shape of the final object.

In a second step, the powder as defined hereinabove or hereinafter is provided. The powder is a prealloyed powder with a particle distribution, i.e. the powder comprises particles of different sizes, and a particle size below 500 um.

In a third step, the powder is poured into the form defining the shape of the component. The form is thereafter sealed, for example by welding. Prior to sealing the form, a vacuum may be applied to the powder mixture, for example by the use of a vacuum pump. The vacuum removes the air from the powder mixture. It is important to remove the air from the powder mixture since air contains argon, which may have a negative effect on ductility of the matrix.

In a fourth step, the filled form is subjected to Hot Isostatic Pressing (HIP) at a predetermined temperature, a predetermined isostatic pressure and a for a predetermined time so that the particles of the alloy bond metallurgical to each other. The form is thereby placed in a heatable pressure chamber, normally referred to as a Hot Isostatic Pressing-chamber (HIP-chamber).

The heating chamber is pressurized with gas, e.g. argon gas, to an isostatic pressure in excess of 500 bar. Typically, the isostatic pressure is above 900-1100 bar, such as 950-1100 bar, and most preferably around 1000 bar. The chamber is heated to a temperature that is selected to below the melting point of the material. The closer the temperature is to the melting point, the higher is the risk for the formation of melted phases in which brittle streaks could be formed. However, at low temperatures, the diffusion process slows down and the HIP:ed material will contain residual porosity and the metallic bond between materials become weak. Consequently, the temperature is in the range of 1000-1200° C., preferably 1100-1200° C., and most preferably around 1150° C. The form is held in the heating chamber at the predetermined pressure and the predetermined temperature for a predetermined time period. The diffusion processes that take place between the powder particles during HIP:ing are time dependent so long times are preferred. Therefore the duration of the HIP-step, once said pressure and temperature has been reached, is in the range of 1-5 hours.

After HIP:ing the form is stripped from the consolidated component. The final product may after the stripping be heat treated.

In this respect the invention, in another embodiment, relates to a method of manufacturing an object of a ferritic-austenitic alloy, comprising the steps of:

a) providing a form defining at least a portion of the shape of said object; providing a powder mixture comprising in percentages by weight:

| | |
|---|---|
| C | 0-0.05; |
| Si | 0-0.8; |
| Mn | 0-4.0; |
| Cr | more than 29-35; |
| Ni | 3.0-10; |
| Mo | 0-4.0; |
| N | 0.30-0.55; |
| Cu | 0-0.8; |
| W | 0-3.0; |
| S | 0-0.03; |
| Ce | 0-0.2; | the balance being Fe and unavoidable impurities;

b) filling at least a portion of said form with said powder mixture;

c) subjecting said form to hot isostatic pressing at a predetermined temperature, a predetermined isostatic pressure and for a predetermined time so that the powder particles bond metallurgically to each other.

It will be understood that the objects made in accordance with the invention as described hereinbefore and hereinafter are not limited to liquid distributors. In fact, the ferritic-austenitic alloy as defined hereinabove or hereinafter and the HIP method as described hereinabove or hereinafter may also be used to manufacture any suitable object which needs to fulfill the same requirements as mentioned hereinabove or hereinafter. The added benefit of the present invention will be particularly enjoyed in the event of objects that are to be used in a highly corrosive environment and that, similar to the aforementioned liquid distributors, contain surfaces that are prone to cross-cut end-attack.

A particular highly corrosive environment is that of the high pressure synthesis section in a urea production plant. As discussed, one of the parts in such a synthesis section where the present invention finds particularly good usage, are the liquid distributors used in the stripper. However, the present invention can also advantageously be used to manufacture other components for the same type of synthesis section.

These other components include radar cones amongst others. This refers to the use of radar for the measurement of liquid level in a urea reactor or in the high pressure stripper. These radar level measuring systems are equipped with a radar cone which is exposed to the corrosive environment prevailing in the said applications. The radar cone itself represents a machined surface that can thus be further improved in respect of corrosion-resistance, by being made in accordance with the present invention.

Yet another area of application in urea plants is the body of high pressure (control) valves or the body of a high pressure ejector. In order to produce the bodies of the high pressure (control) valve or high pressure ejector from corrosion-resistant ferritic-austenitic steel, machining, drilling, or a combination thereof is required. Accordingly, also these parts are vulnerable to cross cut end attack.

Thus, the invention, in this aspect, relates to the use of an object according to the invention as described above, or as produced by a method as described above, as a construction material for a component for a urea manufacturing plant. Therein the component is intended to be in contact with a carbamate solution, and comprises one or more machined surfaces.

Said use as a construction material, in one embodiment, is realized by making the object according to the invention such that it largely, or exactly, has the shape of the component for which it is to be used. Typically, as in the case of liquid distributors (or also in radar cones, and in respect valve bodies), this may mean that the shape is predetermined, and that only holes have to be drilled into the object as produced by HIP. Alternatively, the object produced is just a block (or any other indifferent shape), upon which the desired final component can be made by employing various machining techniques, such as turning, threading, drilling, sawing and milling, or a combination thereof, such as milling or sawing followed by drilling. This can be particularly suitable in the event that the final component has a relatively simple shape, such as a valve body.

The invention, in a further aspect, also pertains to the aforementioned components. Particularly, this refers to a component selected from the group consisting of a liquid distributor, an instrument housing exposed to corrosive liquid, such as a radar cone, a valve body or body of an ejector. Preferably, the invention provides a liquid distributor for a carbamate stripper in a urea manufacturing plant, the liquid distributor being an object in accordance with the invention as defined above, in any of the described embodiments, or as produced by the above process of the invention, in any of the described embodiments.

It will be understood that the invention provides particular benefits for the construction of urea plants. In this aspect, the invention thus also pertains to a plant for the production of urea. Said plant comprises a high pressure urea synthesis section comprising a reactor, a stripper, and a condenser, wherein the stripper comprises liquid distributors according to the invention as described hereinbefore. Similarly, the invention provides urea plants comprising one or more other components obtainable by subjecting corrosion resistant duplex steel, particularly as defined above, to HIP. Such components particularly are radar cones or bodies of (control) valves as well as ejectors.

The urea plant can be a so-called grass-roots plant, i.e. one built as new. However, the invention also finds particular usage, with great benefit, when it comes to modifying an existing plant for the production of urea, especially where the existing plant has been made such as to employ corrosion-resistant duplex steel in those parts, notably in the high-pressure synthesis section of such a plant, that come into contact with highly corrosive carbamate, under the highly corrosive conditions under which the plant is operated. The HIPed ferritic-austenitic steel alloy as defined hereinabove or hereinafter cannot only be used in an existing plant which is constructed in conventional fully austenitic stainless steels but also in plants constructed using high reactive materials such as titanium or zirconium.

In this respect, the present invention provides a method of modifying an existing plant for the production of urea, said plant comprising a stripper, the tubes and liquid distributors of which are made from a corrosion-resistant ferritic-austenitic steel comprising, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities; the method comprising replacing the liquid distributors by liquid distributors according to the invention as described hereinbefore or hereinafter, i.e. obtainable by subjecting corrosion resistant duplex steel, particularly as defined above, to Hot Isostatic Pressing. In a similar aspect, the invention also pertains to modifying such an existing urea plant, by replacing any desired component made of corrosion-resistant ferritic-austenitic steel by a component as described in accordance with the present invention. This particularly refers to components comprising one or more machined surfaces, and preferably selected from the group consisting of a liquid distributor, a radar cone, and a valve body.

It is expressly foreseen that the invention, in all of its aspects as described hereinbefore, including but not limited to the use as a construction material for a component for a urea manufacturing plant and including but not limited to the method of modifying an existing plant for the production of urea, can be realized with reference to all of the embodiments mentioned for the elementary composition of the ferritic-austenitic alloy as described hereinbefore, or hereinafter.

The foregoing plants are described with reference to its main high-pressure synthesis section components. The skilled person is fully aware of which components are generally present in such plants, and how these components are placed relative to each other and in connection with each other. Reference is made to Ullmann's Encyclopedia of Industrial Chemistry, Vol 37, 2012, pp 657-695.

Where in this description embodiments are discussed, combinations of such embodiments, also if discussed separately, are expressly foreseen according to the invention.

The invention is further illustrated with reference to the non-limiting figures and examples discussed hereinafter. In the Examples, a ferritic-austenitic alloy is subjected to hot isostatic pressing (HIP) generally as follows:

In a first step, a form is provided. The form, also referred to as mold or capsule, defines at least a portion of the shape or contour of the final object. The form can be made of steel sheets, e.g. steel sheets which are welded together.

In a second step, the alloy as defined hereinabove or hereinafter in is provided in the form of a powder mixture. It is to be understood that the powder mixture comprises particles of different sizes.

In a third step, the powder mixture is poured into the form that defines the shape of the object. In a forth step, the filled form is subjected to HIP at a predetermined temperature, a predetermined isostatic pressure and for a predetermined tune so that the particles of the alloy are bound metallurgically to each other.

EXAMPLE 1

In this Example, samples of ferritic-austenitic alloys are provided which have been produced by different production methods. The samples are subjected to an investigation of their microstructure.

Five samples were selected. Four samples were of the grade Safurex, and one additional was of the grade SAF 2507 (ex Sandvik) produced by the HIP method. A list of the samples can be seen in Table 1.

TABLE 1

List of the samples used in the investigation

| Sample | Grade | Product | Production method |
|---|---|---|---|
| 1 | SAP 2507 | Bar ø 70 mm | HIP |
| 2 | Safurex | Bar ø 60 mm | HIP |
| 3 | Safurex | Tube 25 × 2.5 mm | Pilgered |
| 4 | Safurex | Bar ø 120 mm | Rolled |
| 5 | Safurex | Tube 37 × 6 mm | Extruded |

Metallographic specimens were prepared from the mentioned samples. The specimens were prepared according to ASTM E 3-01[1] (preparation method 2 for harder materials was used). Three sections were cut from each sample in different directions; transverse section, radial longitudinal section, and tangential longitudinal section according to the suggested designation mentioned in ASTM E 3. The specimens were etched for up to 30 seconds in modified Murakami's reagent, thereby coloring the ferrite phase. The etchant was prepared by mixing 30 g KOH and 30 g $K_3Fe(CN)_6$ in 60 ml $H_2O$, and was left to cool down to room temperature (20° C.) before use.

Sample 2 was prepared according to the following non-limiting example. The alloy as defined hereinabove or hereinafter is gas atomised to form spherical powder particles that are sieved to a size below 500 μm.

The prealloyed powder is poured into a form consisting of welded sheet metal. A vacuum is drawn in the filled mould after which the mould is sealed by welding. Thereafter the mould is placed in a heatable pressure chamber, i.e. Hot Isostatic Pressing-chamber (HIP-chamber). The heating chamber was pressurized with argon gas to an isostatic pressure 1000 bar. The chamber was heated to a temperature of about 1150° C. and the sample was held at that temperature for 2 hours. After HIP:ing the HIPed component is heat treated at a temperature providing the desired phase balance which can be obtained in a phase diagram of the alloy. The heat treatment is performed for 2 hours followed by immediate quenching in water. After heat treatment the mould is removed by machining.

Three different measurements were performed on the prepared specimens;

1. Austenite spacing according to DNV-RP-F112, section 7 (2008) [2]. The picture was oriented with the direction of elongation horizontally and the lines at which the measurements were made where oriented vertically in the picture.

2. Austenite spacing ratio, defined as the ratio between the austenite spacing measured parallel to the elongation direction and the austenite spacing measured perpendicular to the elongation direction (the normal procedure is to measure austenite spacing perpendicular to the direction of elongation). The measurements were performed according to DNV-RP-F112 with the deviation that only one frame was used on each specimen.

3. Average austenite phase length/width ratio. The average austenite phase length/width ratio was measured according to the following procedure;

a. The type of frame used for austenite spacing (DNV-RP-F112) was used.
   b. A cross-grid was projected over the image to produce between 20 and 40 grid crossings.
   c. 10 of the grid crossings were randomly selected so that the grid crossing could be clearly identified as being in the austenite phase.
   d. For each of the 10 crossings, for each of the 10 phases the austenite phase/width ratio was determined by measuring the length and the width of the austenite phase, wherein the length is the longest uninterrupted distance when drawing a straight line between two points at the phase boundary (wherein the phase boundary is the transition from a ferritic to austenitic phase or vice versa); and the width is defined as the longest uninterrupted distance measured perpendicular to the length in the same phase.
   e. The average phase austenite length/width ratio was calculated as the numerical average of the austenite phase length/width ratio of the 10 measured austenite phase length/width ratios.

The magnifications and grid distances that were used for the measurements on the different metallographic specimens are given in Table 2.

The method described above may also be used for measuring the ferritic phase and the ferritic-austenitic phase. If e.g. the ferritic-austenitic phase was used in the method as described above, a result of the same magnitude as the one disclosed in Table 2 would be obtained.

TABLE 2

Magnifications and grid distances

| Sample | Mag. | 1. Aust. Sp. | 2. Aust. Sp. R. | 3. Av. Aust. L/W R. |
|---|---|---|---|---|
| 1 | 200× | 90 μm | H 90 μm, V 60 μm | 70 μm, 28 points |
| 2 | 200× | 90 μm | H 90 μm, V 60 μm | 70 μm, 28 points |
| 3 | 400× | 45 μm | H 45 μm, V 30 μm | 35 μm, 28 points |
| 4 | 100× | 180 μm | H 180 μm, V 120 μm | 140 μm, 28 points |
| 5 | 200× | 90 μm | H 90 μm, V 60 μm | 70 μm, 28 points |

For each of the samples 1 to 5, a picture from each of the metallographic specimen is shown in, respectively, FIGS. 1 to 5. Therein, in each figure, three pictures are shown (top, middle, and bottom), corresponding to the above-mentioned sections (transverse section, radial section and tangential longitudinal section).

The austenite spacing was measured on four frames, with a minimum of 50 measurements on each frame. The austenite spacing was measured perpendicular to the direction of elongation when applicable. On all specimens the austenite spacing was measured vertically in the frame. The orientation of the frames relative to the microstructure was in all cases identical with what can be seen in the pictures presented in FIGS. 1 to 5. The average values from the measurements are presented in Table 3.

The austenite spacing ratio was calculated by dividing the austenite spacing measured in perpendicular directions. First the austenite spacing was measured vertically in the picture which corresponds to perpendicular to the elongation in the same way as for the normal austenite spacing measurement. Then the austenite spacing was measured horizontally in the same pictures which correspond to parallel to the direction of elongation. The results front the vertical measurements can be seen in Table 4, and the results from the horizontal measurements can be seen in Table 5

The austenitic spacing ratio between the measurements made parallel and perpendicular to the elongation of the microstructure is shown in Table 6.

The results front the austenitic phase length/width ratio measurements are presented in Table 7. The results are presented as the average austenitic phase length/width ratio where the value is a numerical average of ten measurements for each metallographic specimen.

The austenite spacing measurements show that the HIPed materials have similar austenite spacing in the three directions and in that sense is more isotropic than for instance the tube products.

The austenite spacing ratio shows that the HIPed materials have a more isotropic microstructure (phase distribution) than conventionally made Safurex.

The results of the average austenite phase length/width ratio measurements show that metallographic specimens with an isotropic phase distribution, such as the HIPed and transversal specimens all exhibit values below 3. Specimens with an anisotropic distribution have values above 3 and in many cases higher than that.

TABLE 3

Results from austenite spacing measurements

| Sample | Type | Transverse | Radial longitudinal | Tangential longitudinal |
|---|---|---|---|---|
| 1 | HIP 2507 | 9.9 | 8.6 | 9.0 |
| 9 | HIP | 9.6 | 8.9 | 9.8 |
| 3 | Pilgered | 5.4 | 3.7 | 7.3 |
| 4 | Rolled bar | 24.9 | 23.8 | 24.0 |
| 5 | Extruded | 8.9 | 8.2 | 14.4 |

TABLE 4

Results from austenite spacing measurements (vertical)

| Sample | Type | Transverse | Radial longitudinal | Tangential longitudinal |
|---|---|---|---|---|
| 1 | HIP 2507 | 9.1 | 8.1 | 9.7 |
| 2 | HIP | 10.6 | 9.4 | 9.4 |
| 3 | Pilgered | 4.7 | 3.6 | 5.6 |
| 4 | Rolled bar | 27.4 | 27.5 | 32.4 |
| 5 | Extruded | 10.5 | 8.3 | 15.8 |

TABLE 5

Results from austenite spacing measurements (horizontal)

| Sample | Type | Transverse | Radial longitudinal | Tangential longitudinal |
|---|---|---|---|---|
| 1 | HIP 2507 | 9.1 | 9.7 | 9.5 |
| 2 | HIP | 10.6 | 9.3 | 9.5 |
| 3 | Pilgered | 4.1 | 20.3 | 29 |
| 4 | Rolled bar | 25.8 | 122.5 | 96.7 |
| 5 | Extruded | 10.6 | 40.1 | 43.2 |

TABLE 6

Results from the measurements made parallel and perpendicular to the elongation of the microstructure.

| Sample | Type | Transverse | Radial longitudinal | Tangential longitudinal |
|---|---|---|---|---|
| 1 | HIP 2507 | 1.00 | 1.20 | 0.98 |
| 2 | HIP | 1.00 | 0.99 | 1.01 |
| 3 | Pilgered | 0.87 | 5.64 | 5.18 |
| 4 | Rolled bar | 0.94 | 4.45 | 2.98 |
| 5 | Extruded | 1.01 | 4.83 | 2.73 |

TABLE 7

Average austenite phase length/width ratio. The values are numerical averages from 10 measurements for each specimen.

| Sample | Type | Transverse | Radial longitudinal | Tangential longitudinal |
|---|---|---|---|---|
| 1 | HIP 2507 | 1.7 | 2.1 | 1.8 |
| 2 | HIP | 1.8 | 1.8 | 1.7 |
| 3 | Pilgered | 2.4 | 20.0 | 8.9 |
| 4 | Rolled bar | 2.5 | 4.7 | 8.0 |
| 5 | Extruded | 1.9 | 10.9 | 4.5 |

EXAMPLE 2

Two test samples were provided of steel of grade Safurex. The samples, representing a typical construction as used in liquid distributors, were half rings with three holes drilled in it.

Sample 2HIP was made by a HIP process in accordance with the invention. Sample 2REF was made conventionally by hot extrusion from a bar material, followed by cold pilgering to form a pipe.

The samples were subjected to a Streicher corrosion test. The Streicher test is known in the art as a standardized test for determining the corrosion resistance of a material (ASTM A262-02: Standard Practices for Detecting Susceptibility to Intergranular Attack in Austenitic Stainless Steels; practice B: Sulfate-Sulfuric Acid Test).

Figure 6:
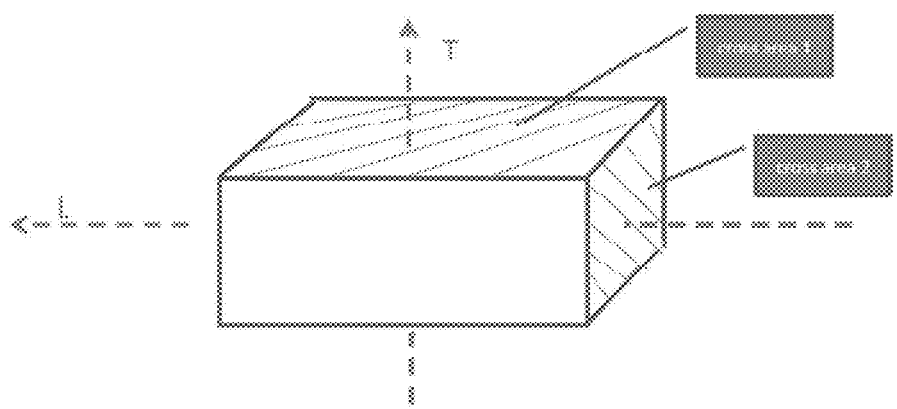
FIG. 6 is a schematic drawing indicating the cross sections applied in Examples 2 and 3.

Subsequently, micro preparations were obtained from the samples. In these samples, the austenite spacing (according to DNV-RP-F112) and the austenite length/width ratio were determined in two directions perpendicular to each other. The latter is shown in FIG. 6. Therein:

L=longitudinal direction (rolling or pilgering direction)
T=Transfer direction (perpendicular to rolling or pilgering direction)
Cross area 1 (CA1) is perpendicular to T direction
Cross area 2 (CA2) is perpendicular to L direction The results are given in Table 8 with reference to weight reduction and selective attack of the material. The HIPed material of the invention shows a substantially lower weight-loss, and a substantially lower selective attack.

Figure 7:
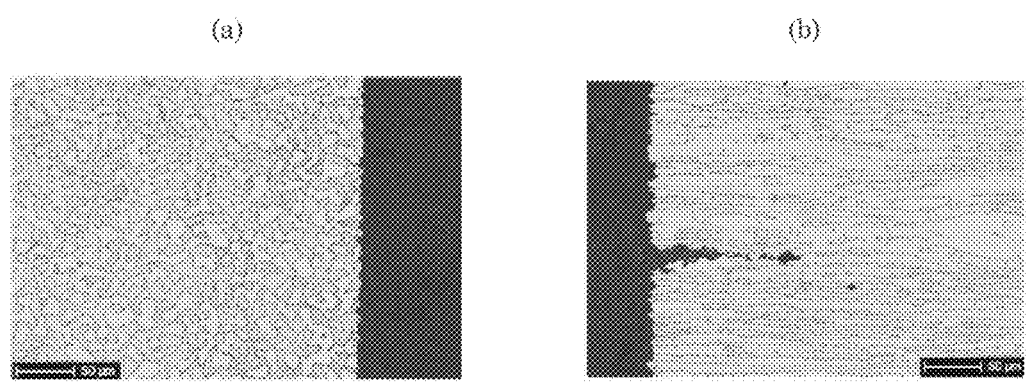
FIG. 7 presents microscopic pictures of cross sections of samples subjected to the corrosion test according to Example 2.

In FIG. 7 microscopic pictures are shown of cross section area 1 (CA1) for:
(a) sample 2HIP;
(b) sample 2REF.

The pictures clearly show that sample 2HIP has hardly been visibly affected by the test conditions, whilst sample 3REF has considerable damage.

TABLE 8

| Streicher Test | Sample 2HIP | Sample 2REF |
|---|---|---|
| Austenite spacing (μm): CA 1 | 13.08 - STD 8.68 | 81.00 STD 59.60 |
| Austenite spacing (μm): CA 2 | 10.98 - STD 8.05 | 11.91 STD 7.23 |
| Weight loss (gr/m2/hr) | 0.44 | 0.73 |
| Selective Attack (μm) | max 4 (FIG. 7a) | max 160 (FIG. 7b) |

EXAMPLE 3

Two samples were prepared as in Example 2.

Sample 3HIP was made by a HIP process in accordance with the invention. Sample 3REF was made conventionally by hot extrusion from a bar material, followed by cold pilgering to form a pipe.

The samples were subjected to conditions as typically encountered in urea production. Accordingly, the samples were submerged in a solution containing urea, carbon dioxide, water, ammonia, and ammonium carbamate. The conditions were as follows:

N/C ratio: 2.9

| Temperature: | 210 | ° C. |
| Pressure: | 260 | Bar |
| Exposure time: | 24 | Hours |
| Oxygen content: | <0.01% | |

Subsequently, micro preparations were obtained from the samples as in Example 2. In these samples, the austenite spacing (according to DNV-RP-F112) and the austenite length/width ratio were determined in two directions perpendicular to each other, again as shown in FIG. 6.

The results are given in Table 9 with reference to weight reduction and selective attack of the material. The HIPed material of the invention shows a substantially lower weight-loss, and no selective attack.

TABLE 9

| Ammomium carbamate test | Sample 3HIP | Sample 3REF |
|---|---|---|
| Austenite spacing (μm): CA 1 | 1.672 | 26.025 |
| Austenite spacing (μm): CA 2 | 1.414 | 4.454 |
| Weight loss (gr/m2/hr) | 0.22 | 0.67 |
| Selective Attack (μm) | none | max 30 |

The invention claimed is:

1. A liquid distributor for a stripper in a urea manufacturing plant, wherein the liquid distributor is prepared from an object obtainable by a process which comprises subjecting a ferritic-austenitic steel alloy powder to hot isostatic pressing, wherein the ferritic-austenitic steel alloy powder consists of, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities.

2. The liquid distributor of claim 1, wherein the ferritic-austenitic steel alloy has an austenite spacing smaller than 20 μm as determined by DNV-RP-F112, Section 7, with sample preparation according to ASTM E 3-01; and wherein said alloy has a largest average austenite phase length/width ratio smaller than 5;

wherein the largest average austenite phase length/width ratio is determined by determining the average austenite phase length/width ratio in three cross-sections of a sample of the ferritic-austenitic steel alloy to give three average austenite phase length/width ratios and selecting the largest one of said three average austenite phase length/width ratios;

wherein in each cross section the austenite phase length/width ratio is determined by the following procedure:

i. preparing the cross-cuts surfaces of the sample;
ii. polishing the surfaces using diamond paste on a rotating disc with a particle size of first 6 μm and subsequently 3 μm to create a polished surface;
iii. etching the surfaces using Murakami's agent for up to 30 seconds at 20° C. thereby coloring the ferrite phase, the agent being provided by preparing a saturated solution by mixing 30 g potassium hydroxide and 30 g K$_3$Fe(CN)$_6$ in 100 ml H$_2$O, and allowing the solution to cool down to room temperature before use;

iv. observing the cross-cut surfaces in etched condition under an optical microscope with a magnification selected such that phase boundaries are distinguishable;
v. projecting a cross-grid over the image, wherein the grid has a grid distance adapted to observe the austenite-ferrite phase boundaries;
vi. randomly selecting at least ten grid crossings on the grid such that the grid crossings can be identified as being in the austenite phase;
vii. determining, at each of the ten grid crossings, the austenite phase length/width ratio by measuring the length and the width of the austenite phase, wherein the length is the longest uninterrupted distance when drawing a straight line between two points at the phase boundary, the phase boundary being the transition from an austenitic phase to the ferrite phase; and wherein the width is defined as the longest uninterrupted distance measured perpendicular to the length in the same phase; and calculating the average austenite phase length/width ratio as the numerical average of the austenite phase length/width ratios of the ten measured austenite phase length/width ratios.

3. The liquid distributor of claim 2, wherein the sample on which the measurement is performed has at least one dimension of greater than 5 mm.

4. The liquid distributor of claim 2, wherein said austenite spacing is smaller than 15 μm.

5. The liquid distributor of claim 1, wherein the elementary composition of the alloy consists of, in percentages by weight:

| | |
|---|---|
| C | 0-0.030; |
| Mn | 0.8-1.50; |
| S | 0-0.03; |
| Si | 0-0.50; |
| Cr | 28.0-30.0; |
| Ni | 5.8-7.5; |
| Mo | 1.50-2.60; |
| W | 0-3.0 |
| Cu | 0-0.80; |
| N | 0.30-0.40 |
| Ce | 0-0.2; | the balance being Fe and unavoidable impurities.

6. The liquid distributor of claim 1, wherein the elementary composition consists of, in percentages by weight:

| | |
|---|---|
| C | 0-0.03; |
| Si | 0-0.5; |
| Mn | 0.3-1; |
| Cr | 29-33; |
| Ni | 3-10; |
| Mo | 1.0-1.3; |
| N | 0.36-0.55; |
| Cu | 0-1.0; |
| W | 0-2.0; |
| S | 0-0.03; |
| Ce | 0-0.2; | the remainder being Fe and unavoidable impurities, the ferrite content being 30-70% by volume.

7. The liquid distributor of claim 1, wherein said liquid distributor comprises drilled holes.

8. A plant for the production of urea, said plant comprising one or more components prepared from an object obtainable by a process which comprises subjecting a ferritic-austenitic steel alloy powder to hot isostatic pressing, wherein the ferritic-austenitic steel alloy powder consists of, in percentages by weight:

| | |
|---|---|
| C | 0-0.05; |
| Si | 0-0.8; |
| Mn | 0-4.0; |
| Cr | 26-35; |
| Ni | 3.0-10; |
| Mo | 0-4.0; |
| N | 0.30-0.55; |
| Cu | 0-1.0; |
| W | 0-3.0; |
| S | 0-0.03; |
| Ce | 0-0.2; | the balance being Fe and unavoidable impurities.

9. The plant of claim 8, wherein the components are selected from the group consisting of liquid distributors, radar cones, (control) valves and ejectors.

10. The plant of claim 9, comprising a high pressure urea synthesis section comprising a stripper, wherein said component is at least one liquid distributor comprised in said stripper.

11. The plant of claim 10, wherein said liquid distributor comprises drilled holes.

12. The plant of claim 8, wherein, the ferritic-austenitic steel alloy has an austenite spacing smaller than 20 μm as determined by DNV-RP-F112, Section 7, with sample preparation according to ASTM E 3-01; and wherein said alloy has a largest average austenite phase length/width ratio smaller than 5;

wherein the largest average austenite phase length/width ratio is determined by determining the average austenite phase length/width ratio in three cross-sections of a sample of the ferritic-austenitic steel alloy to give three average austenite phase length/width ratios and selecting the largest one of said three average austenite phase length/width ratios;

wherein in each cross section the austenite phase length/width ratio is determined by the following procedure:
i. preparing the cross-cuts surfaces of the sample;
ii. polishing the surfaces using diamond paste on a rotating disc with a particle size of first 6 μm and subsequently 3 μm to create a polished surface;
iii. etching the surfaces using Murakami's agent for up to 30 seconds at 20° C. thereby coloring the ferrite phase, the agent being provided by preparing a saturated solution by mixing 30 g potassium hydroxide and 30 g $K_3Fe(CN)_6$ in 100 ml $H_2O$, and allowing the solution to cool down to room temperature before use;
iv. observing the cross-cut surfaces in etched condition under an optical microscope with a magnification selected such that phase boundaries are distinguishable;
v. projecting a cross-grid over the image, wherein the grid has a grid distance adapted to observe the austenite-ferrite phase boundaries;
vi. randomly selecting at least ten grid crossings on the grid such that the grid crossings can be identified as being in the austenite phase;
vii. determining, at each of the ten grid crossings, the austenite phase length/width ratio by measuring the length and the width of the austenite phase, wherein the length is the longest uninterrupted distance when drawing a straight line between two points at the phase boundary, the phase boundary being the transition from an austenitic phase to the ferrite phase; and wherein the width is defined as the longest uninterrupted distance measured perpendicular to the length in the same phase;
calculating the average austenite phase length/width ratio as the numerical average of the austenite phase length/width ratios of the ten measured austenite phase length/width ratios.

13. The plant of claim 12, wherein the sample on which the measurement is performed has at least one dimension of greater than 5 mm.

14. The plant of claim 12, wherein said austenite spacing is smaller than 15 μm.

15. The plant of claim 12, wherein the elementary composition of the alloy consists of, in percentages by weight:

| | |
|---|---|
| C | 0-0.030; |
| Mn | 0.8-1.50; |
| S | 0-0.03; |
| Si | 0-0.50; |
| Cr | 28.0-30.0; |
| Ni | 5.8-7.5; |
| Mo | 1.50-2.60; |
| W | 0-3.0 |
| Cu | 0-0.80; |
| N | 0.30-0.40 |
| Ce | 0-0.2; | the balance being Fe and unavoidable impurities.

16. The plant of claim 12, wherein the elementary composition consists of, in percentages by weight:

| | |
|---|---|
| C | 0-0.03; |
| Si | 0-0.5; |
| Mn | 0.3-1; |
| Cr | 29-33; |
| Ni | 3-10; |
| Mo | 1.0-1.3; |
| N | 0.36-0.55; |
| Cu | 0-1.0; |
| W | 0-2.0; |
| S | 0-0.03; |
| Ce | 0-0.2; | the remainder being Fe and unavoidable impurities, the ferrite content being 30-70% by volume.

* * * * *